United States Patent
Frauenkron et al.

(10) Patent No.: US 6,958,397 B2
(45) Date of Patent: Oct. 25, 2005

(54) METHOD OF SELECTIVELY SYNTHESIZING TRIETHYLENEDIAMINE

(75) Inventors: Matthias Frauenkron, Ludwigshafen (DE); Bernd Stein, Alsbach-Hähnlein (DE); Ortmund Lang, Quirnbach (DE)

(73) Assignee: BASF AG, Ludwigshafen (DE)

( * ) Notice: Subject to any disclaimer, the term of this patent is extended or adjusted under 35 U.S.C. 154(b) by 40 days.

(21) Appl. No.: 10/482,644

(22) PCT Filed: Jul. 4, 2002

(86) PCT No.: PCT/EP02/07430

§ 371 (c)(1),
(2), (4) Date: Jan. 5, 2004

(87) PCT Pub. No.: WO03/004499

PCT Pub. Date: Jan. 16, 2003

(65) Prior Publication Data

US 2004/0236106 A1 Nov. 25, 2004

(30) Foreign Application Priority Data

Jul. 5, 2001 (DE) ........................ 101 32 499

(51) Int. Cl.[7] .......................................... C07D 487/08
(52) U.S. Cl. ..................................................... 544/352
(58) Field of Search ......................................... 544/352

(56) References Cited

U.S. PATENT DOCUMENTS

| | | | | | |
|---|---|---|---|---|---|
| 3,956,329 | A | * | 5/1976 | Murakami et al. | 544/352 |
| 4,804,758 | A | * | 2/1989 | Hoelderich et al. | 544/352 |
| 5,731,449 | A | * | 3/1998 | Li et al. | 544/352 |
| 5,741,906 | A | * | 4/1998 | Santiesteban et al. | 544/352 |
| 6,084,096 | A | * | 7/2000 | Li et al. | 544/352 |

FOREIGN PATENT DOCUMENTS

EP 312734 * 4/1989 ......... C07D/487/08

\* cited by examiner

*Primary Examiner*—Brian Davis
(74) *Attorney, Agent, or Firm*—Novak Druce & Quigg, LLP

(57) ABSTRACT

The present invention describes a process for the preparation of triethylenediamine by reacting piperazine over a zeolite catalyst which, in addition to $SiO_2$, contains an oxide of at least one further divalent, trivalent or tetravalent metal M, wherein the zeolite has a molar Si/M ratio of >100. In particular, a zeolite of the ZSM-5 type is used. The use of the zeolites permits suppression of the undesired formation of the byproduct 2-ethylpiperazine and hence considerable simplification of the working-up, in combination with high piperazine conversions and a small excess of water.

18 Claims, No Drawings

METHOD OF SELECTIVELY SYNTHESIZING TRIETHYLENEDIAMINE

The present invention relates to a selective process for the preparation of triethylenediamine (TEDA) from piperazine (PIP), in which a zeolite of a specific composition is used as a catalyst.

TEDA (IUPAC name: 1,4-diazabicyclo[2.2.2]octane) is an important intermediate and end product in the chemical industry, which is used mainly as such as a catalyst in the preparation of polyurethanes. A large number of different syntheses which differ mainly in the choice of the starting materials and of the catalysts used are available for the preparation of TEDA.

On the one hand, it is possible to use a range of different starting materials which contain a C2 building block and/or a nitrogen building block and may be cyclic or acyclic. Examples of suitable starting materials include ethylenediamine, diethylenetriamine, ethanolamine, aminoethylethanolamine, piperazine, aminoethylpiperazine and hydroxyethylpiperazine. A single starting material is frequently used, but mixtures of two or more suitable starting materials may also advantageously be used. Usually, water is also added to the reaction mixture. The composition of the product mixture is decisively influenced by the choice of the starting materials, the avoidance of the formation of byproducts, in addition to the availability of the starting materials, being an important aspect with regard to the specification to be achieved in the working-up. In most cases, in order to increase the selectivity with respect to the desired product TEDA, the synthesis is carried out so that only a partial conversion of the starting material or starting materials used occurs. The disadvantage of the low yield is accepted because of the small amounts of undesired byproducts which could be achieved.

On the other hand, it is possible to use different catalysts, for example noncrystalline phosphates and silicates of different origin, but in particular zeolites. A broad variation with regard to characteristic parameters, for example the composition, pretreatment, acidity or pore size, is also possible in the case of the zeolites. For example, in addition to the classical zeolites consisting of $SiO_2$ and $Al_2O_3$, it is also possible to use those which contain, for example, B, Ti, Ga or oxides of other elements. In the case of the zeolite catalysts, too, their use depends in principle on the selectivities which can be achieved with them.

An advantageous starting material for the TEDA preparation, owing to its formation in the ethylenediamine synthesis, is piperazine (PIP), to which an ethylene group must also be added in order to obtain TEDA. In order to provide this building block, PIP is frequently reacted as a mixture with a further starting material, which contains the building block, in the TEDA synthesis. This further starting material may be, for example, ethanolamine, ethylenediamine or monoethylene glycol. Alternatively, a substituted piperazine which contains the C2 building block in the substituent, for example aminoethylpiperazine or hydroxyethylpiperazine, is also frequently used, mixtures of such a substituted piperazine with unsubstituted piperazine also being used in one variant.

On the one hand, however, the use of mixtures of different starting materials is disadvantageous for process engineering reasons since the product mixtures obtainable therefrom have a more complicated composition than with the use of individual starting materials and often have to be separated by an expensive procedure. On the other hand, substituted piperazines are generally prepared from unsubstituted piperazines, so that it is desirable to be able to use piperazine as a single starting material. This is possible in principle and is known, but conversion and selectivity principally have lower values than with the use of, for example, a mixture of different starting materials. In order to solve this problem, for example, EP-A 312 734 discloses a process for the preparation of TEDA, in which PIP is used as the only starting material and the zeolite catalyst used is of the formula

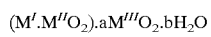

where
$M^I$ is one equivalent of a monovalent alkali metal ion, a proton, an ammonium group or half an equivalent of a divalent alkaline earth metal cation,
$M^{II}$ is one equivalent of $Al^{3+}$, $B^{3+}$, $Sb^{3+}$, $As^{3+}$, $Cr^{3+}$, $V^{3+}$, $Ga^{3+}$ or $Fe^{3+}$,
$M^{III}$ is one equivalent of $Si^{4+}$, $Ge^{4+}$, $Ti^{4+}$ or $Zr^{4+}$,
a is from 15 to 200 and
b is from 0 to 8.

The catalyst used preferably has a pentasil structure, in particular a ZSM-5 structure. Regarding the composition of such a zeolite, it is preferable if $M^I$ is a proton, $M^{II}$ is $B^{3+}$ or preferably $Al^{3+}$ and $M^{III}$ is $Ge^{4+}$ or preferably $Si^{4+}$.

It is true that the process disclosed in EP-A 312 734 permits high selectivities of up to about 90% with respect to TEDA, as is evident from the examples. However, a certain amount of 2-ethylpiperazine (EtPIP) always forms as a byproduct, which is extremely difficult to separate from TEDA. By using low reaction temperatures, the formation of EtPIP can be reduced to very low values, but this is achieved at the expense of a very low conversion. Thus, it is possible according to example 3 to carry out the process so that only 0.21% of EtPIP (corresponding to a selectivity of 0.21%) is formed. Such selectivities are in a range which is acceptable for a process on the industrial scale. However, the PIP conversion is only 18%, which in turn is substantially too low.

It is an object of the present invention to provide a process which permits the production of TEDA from PIP with high conversions and selectivities with respect to TEDA and formation of only little EtPIP.

We have found that this object is achieved by a process for the preparation of TEDA by reacting PIP over a zeolite which, in addition to $SiO_2$, contains at least one further oxide of at least one divalent, trivalent or tetravalent metal M, wherein the zeolite has a molar Si/M ratio of >100.

It has been found that the formation of EtPIP in the synthesis of TEDA from PIP is suppressed by the use of the zeolites described above. The use of the zeolite makes it possible to carry out the process at temperatures which are above those used according to EP-A 312 734, with the result that the PIP conversion increases without undesired large amounts of EtPIP being formed.

The zeolites used according to the invention contain in their skeleton, in addition to $SiO_2$, one or more oxides of a metal M in the oxidation state II, III or IV, i.e. oxides having the composition $M^{II}O$, $M^{III}_2O_3$ and/or $M^{IV}O_2$. An important characteristic of the zeolites used according to the invention is the molar ratio of Si to the metal M, i.e. the modulus, which is >100, preferably >200, more preferably from >300 to 40 000, in particular from 400 to 5 000.

The upper limit of the modulus (40 000) is determined only by the purity of the starting substances (residual traces of M or compounds of M) and the cleanliness and chemical resistance of the apparatuses used in the synthesis of the zeolite.

At a modulus below the stated limit, the Bronsted and Lewis acidity density (acidity density: acid centers/total catalyst surface area) of the zeolites increases substantially, the achievable TEDA yield and selectivity and the catalyst on-stream time decrease substantially and the cost of purifying the TEDA increases substantially.

Surprisingly, it has been found that the advantages according to the invention, for example a substantial improvement in the selectivity with respect to TEDA, are achieved by the dramatic reduction in the acidity within the zeolite crystal in the novel process, which is produced by incorporating divalent and/or trivalent metals in the form of metal oxides in the lattice, usually during the hydrothermal synthesis. According to the invention, zeolites having tetravalent metals in the form of metal oxides in the zeolite lattice also achieve improved selectivity with respect to TEDA.

For the zeolite catalyst, preferably of the Pentasil type, having moduli as above, there are no additional requirements either with respect to the zeolite material as such or with respect to the process by which this is obtainable.

In the zeolite catalyst which is used in the novel process and contains one or more metals M in the oxidation state II, III or IV as oxides in addition to $SiO_2$, the metal M in the oxidation state II is preferably selected from the group consisting of Zn, Sn and Be and mixtures thereof, the metal M in the oxidation state III is preferably selected from the group consisting of Al, B, Fe, Co, Ni, V, Mo, Mn, As, Sb, Bi, La, Ga, In, Y, Sc and Cr and mixtures thereof, and the metal M in the oxidation state IV is preferably selected from the group consisting of Ti, Zr, Ge, Hf and Sn and mixtures thereof.

Zeolites in which M is aluminum, gallium, titanium, zirconium, germanium, iron or boron are preferred. Those in which M is aluminum, titanium, iron or boron are particularly preferred.

For example, the following types are suitable as zeolite catalysts of the Pentasil type which are to be used according to the invention: ZSM-5 (as disclosed, in U.S. Pat. No. 3,702,886), ZSM-11 (as disclosed, for example, in U.S. Pat. No. 3,709,979), ZSM-23, ZSM-53, NU-87, ZSM-35, ZSM-48 and mixed structures comprising at least two of the abovementioned zeolites, in particular ZSM-5 and ZSM-11, and mixed structures thereof.

Zeolites having the MFI or MEL structure or the MEL/MFI or MFI/MEL mixed structure are particularly preferred for the novel process.

The zeolites used according to the invention are crystalline metal silicates having an ordered channel and cage structure and possessing micropores. The network of such zeolites is composed of $SiO_4$ tetrahedra and $M_{2/z}O$ (z=2, 3 or 4) tetrahedra which are linked via common oxygen bridges. An overview of the known structures is given, for example, by W. M. Meier, D. H. Olsen and Ch. Baerlocher in Atlas of Zeolite Structure Types, Elsevier, 4th Edition, London 1996.

According to the invention, it is also possible to use zeolites which contain no aluminum (M=Al) and in which some of the Si(IV) in the zeolite lattice has been replaced by a metal M(IV), e.g. Ti, Zr, Ge, Hf and/or Sn, and some by a metal M(II), e.g. Zn, Sn and/or Be, and/or some by a metal M(III), e.g. B, Fe, Co, Ni, V, Mo, Mn, As, Sb, Bi, La, Ga, In, Y, Sc and/or Cr.

(II=Oxidation state 2, III=oxidation state 3, IV=oxidation state 4).

Usually, said zeolites are prepared by reacting a mixture of an $SiO_2$ source and of a metal source (e.g. M=Al, Zn, Be, B, Fe, Co, Ni, V, Mo, Mn, As, Sb, Bi, La, Ga, In, Y, Sc, Cr, Ti, Zr, Ge, Hf and/or Sn in the oxidation states as described above) and in a nitrogen-containing base as a template, e.g. tetraalkylammonium salt, if required also with the addition of basic compounds (e.g. alkalis), in a pressure-resistant container at elevated temperatures over a period of several hours or a few days, a crystalline product being formed. This is separated off (for example filtered off, spray-dried or precipitated), washed, dried and calcined at elevated temperatures to remove the organic nitrogen base (see below). Alternatively, the synthesis is also possible without a template, provided that the formation of the zeolite is ensured. In the powder thus obtained, the metal (e.g. M=Al, Zn, Be, B, Fe, Co, Ni, V, Mo, Mn, As, Sb, Bi, La, Ga, In, Y, Sc, Cr, Ti, Zr, Ge, Hf and/or Sn in the oxidation states as described above) is present at least partly in varying amounts with 4-, 5- or 6-fold coordination within the zeolite lattice.

The zeolites used according to the invention are prepared by the process described and/or are commercially available.

If, as a result of the method of production, the zeolite catalyst to be used according to the invention, preferably of the Pentasil type, is not present at least partly in the preferred acidic $H^+$ form and/or $NH_4^+$ form but, for example, in the $Na^+$ form (or any other metal salt form), it can be converted at least partly into the preferred $H^+$ and/or $NH_4^+$ form, according to the prior art, by ion exchange, for example with ammonium ions, and subsequent calcination (see below). The treatment with dilute protic acids, e.g. mineral acid, for converting the zeolite at least partly into the $H^+$ form is likewise known from the literature and is just aas feasible. All protic acids, e.g. hydrochloric acid or sulfuric acid, are suitable here (see below).

It is then possible to convert the zeolite catalysts, subjected to exchange in this manner, into a desired $Me^+$ form which still contains $H^+$ and/or $NH_4^+$, by ion exchange with a corresponding metal salt solution (metal Me=alkali metal, alkaline earth metal, transition metal).

In order to achieve very high selectivity, high conversions and particularly long catalyst on-stream times, it may be advantageous to modify the zeolite catalysts as claimed in the claims.

A suitable modification of the zeolite catalysts consists, as described in J. Weitkamp et al., Catalysis and Zeolites, Chapter. 3: Modification of Zeolites, Springer Verlag, 1999, in subjecting the zeolite material—in molded or unmolded form—to a treatment, according to the known prior art (EP-A-382 055, page 4, line 2 et seq.+line 20 et seq.; DE-C2-24 34 913, page 3, line 23 et seq.; U.S. Pat. No. 5,041,548, page 4, line 27 et seq.), with concentrated or dilute protic acids, e.g. hydrochloric acid, sulfuric acid, hydrofluoric acid, phosphoric acid or a carboxylic acid, dicarboxylic acid or polycarboxylic acid—and/or complexing agents, e.g. acetylacetonate (acac), nitrilotriacetic acid, sulfosalicylic acid or ethylenediaminetetraacetic acid (EDTA)—for example according to EP-A-842 936 and RU-C1-21 14 849, and/or steam.

In a particular embodiment, the zeolites used in the process of the invention can be doped by applying transition metals of subgroups I to VIII, preferably those of subgroups I, II, IV and VIII, particularly preferably Zn, Ti, Zr, Fe, Co, Ni, Cr or V.

The application can be achieved by impregnating the zeolite used in the novel process in aqueous metal salt solutions, by spraying corresponding metal salt solutions onto the zeolite or by other suitable processes known in the prior art. Suitable metal salts for the preparation of the metal salt solutions are the nitrates, nitrosylnitrates, halides, carbonates, carboxylates, acetylacetonates, chloro complexes, nitro complexes or amino complexes of corresponding metals, the nitrates and nitrosylnitrates being preferred. In the case of zeolites which are doped with a plurality of metals, the metal salts or metal salt solutions can be applied simultaneously or in succession.

The zeolites coated or impregnated with the metal salt solutions are then dried, preferably at from 60 to 150° C., and if desired calcined at from 200 to 950° C., preferably from 400 to 750° C. In the case of separate application by impregnation, the catalyst is dried after each impregnation step and if desired calcined as described above. The sequence in which the transition metals are applied by impregnation can be freely chosen. If desired, the coated and dried and, if desired, calcined zeolites are then activated by treatment in a gas stream which contains free hydrogen, at from 30 to about 600° C., preferably from 150 to about 450° C. Preferably, the gas stream consists of from 50 to 100% by volume of hydrogen and from 0 to 50% by volume of nitrogen.

The transition metal solutions are applied to the zeolite in an amount such that the total content of transition metal is from about 0.01 to about 10, preferably from about 0.01 to 5, more preferably from about 0.01 to about 2, in particular from about 0.05 to 1, % by weight, based in each case on the total weight of the catalyst.

The transition metal surface area on the catalyst is altogether preferably from about 0.01 to about 10, more preferably from about 0.05 to 5, in particular from about 0.05 to 3, $m^2/g$ ($m^2$ per g of the catalyst). The metal surface is determined by means of the chemisorption method described by J. LeMaitre et al. in Characterization of Heterogeneous Catalysts, Editor Francis Delanny, Marcel Dekker, New York 1984, pages 310–324.

In order to increase the mechanical stability, the zeolites to be used according to the invention can be supported, for example on cellulose materials, clays, polymers, metals, graphite, binders or metal oxides, such as clays, alumina or silica. Furthermore, it is possible to use them in the form of granules, in spherical form or applied to glass bodies or other bodies, e.g. fabrics (in particular metal fabrics) of any kind.

In principle, all methods for obtaining a corresponding shape can be used as strength-imparting shaping processes for the zeolites to be used according to the invention. Methods in which the shaping is effected by tabletting or extrusion are preferred. Methods in which the shaping is effected by extrusion in conventional extruders, for example to give extrudates having a diameter of, usually, from 1 to 10 mm, in particular from 2 to 5 mm, are particularly preferred. If binders and/or assistants are required, the extrusion or the tabletting is expediently preceded by a mixing or kneading process. If required, the extrusion/tabletting is also followed by a calcination step. The moldings obtained are, if desired, comminuted, preferably to give granules or chips having a particle diameter of from 0.5 to 5 mm, in particular from 0.5 to 2 mm. These granules or these chips and also catalyst moldings produced in other ways contain virtually no particle fractions finer than those having a minimum particle diameter of 0.5 mm.

In a preferred embodiment, the shaped zeolite to be used according to the invention contains up to 80% by weight, based on the total mass of the catalyst, of binder. Particularly preferred binder contents are from 1 to 60, in particular from 20 to 45, % by weight. Suitable binders are in principle all compounds used for such purposes, compounds, in particular oxides, of silicon, of aluminum, of boron, of phosphorus, of zirconium and/or of titanium being preferred. Of particular interest as a binder is silica, it also being possible to introduce the $SiO_2$ in the form of silica sol or in the form of tetraalkoxysilanes into the shaping process. Oxides of magnesium and of beryllium and clays, e.g. montmorillonite, kaolins, bentonites, halloysites, dickites, nacrites and anauxites, can also be used as binders.

Examples of assistants for the strength-imparting shaping processes are extrusion assistants for the extrusion, a conventional extrusion assistant being methylcellulose. Such agents undergo complete combustion as a rule in a subsequent calcination step.

The calcination of the zeolite catalyst to be used according to the invention is effected at from 250 to 950° C., preferably from 400 to 750° C., particularly preferably from 450 to 600° C., for the duration of, in general, at least one hour, preferably for 2–5 hours. The calcination is effected in a gas atmosphere, for example a nitrogen, air or noble gas atmosphere. As a rule, calcination is effected in an oxygen-containing atmosphere, the oxygen content being from 0.1 to 90, preferably from 0.2 to 22, particularly preferably from 10 to 22, % by volume. The use of other oxygen-donating substances is also possible. The above term oxygen-donating substances includess all substances which are capable of releasing oxygen under the stated calcination conditions. Particular examples are oxides of nitrogen of the formula $N_xO_y$, where x and y are chosen so that a neutral oxide of nitrogen results, $N_2O$ and $N_2O$-containing exit gas stream from an adipic acid part, NO, $NO_2$, ozone or a mixture of two or more thereof. When $CO_2$ is used as the oxygen-donating substance, temperatures of from 500° C. to 800° C. are preferably established in the calcination. Calcination under a steam atmosphere is also possible.

According to the invention, it is furthermore recognized that, after the use of the zeolite catalyst to be used according to the invention, said catalyst can be regenerated, independently of its form, for example after a decrease in the activity and/or in the selectivity, by a process in which the regeneration is effected by specific burning-off of the coatings responsible for the deactivation. It is preferable to employ an inert gas atmosphere which contains the exactly defined amounts of oxygen-donating substances. Such a regeneration process is described, inter alia, in WO 98/55228 and DE-A1-19 72 39 49, the disclosure of which is hereby incorporated by reference in its entirety in the present application.

After the regeneration, the activity and/or the selectivity of the catalyst increases compared with the state immediately before the regeneration.

The zeolite catalyst to be regenerated and to be used according to the invention is heated either in the reaction apparatus (reactor) or in an external oven in an atmosphere which contains from 0.1 to about 20 parts by volume of oxygen-donating substances, particularly preferably from 0.1 to about 20 parts by volume of oxygen, to a temperature in the range of from about 250 to 800° C., preferably from about 400° C. to 550° C., in particular from about 450° C. to 500° C. The heating-up is preferably carried out at a heating rate of from about 0.1 to about 20, preferably from about 0.3 to about 15, in particular from 0.5 to 10, ° C./min.

In the heating-up phase, the catalyst is heated to a temperature at which the generally organic coatings present there begin to decompose, while at the same time the temperature is regulated by means of the oxygen content and thus does not increase so that the catalyst structure is damaged. The slow increase in the temperature or dwelling at low temperature by establishing the corresponding oxygen content and the corresponding heating power is a substantial step towards preventing local overheating of the catalyst in the case of high organic loads of the catalyst to be regenerated.

If the temperature of the exit gas stream at the reactor outlet decreases in spite of increasing amounts of oxygen-donating substances in the gas stream, burning-off of the organic coatings is complete. The duration of the treatment is in each case generally from about 1 to 30, preferably from about 2 to about 20, in particular from about 3 to about 10, hours.

On subsequent cooling of the catalyst thus regenerated, it should be ensured that the cooling does not take place too rapidly (quenching), since otherwise the mechanical strength of the catalyst may be adversely affected.

It may be necessary to subject the catalyst, after the regeneration by calcination has been carried out, as described above, to wash it with water and/or dilute acid, e.g. hydrochloric acid, in order to remove any inorganic catalyst load (traces of alkali, etc.) remaining as a result of contamination of the starting materials. Further drying and/or calcination of the catalyst can then be carried out.

In a further embodiment of the novel process, the catalyst which has been at least partly deactivated is washed, according to the regeneration procedure and before heating, with a solvent in the reaction reactor or in an external reactor, in order to remove any desired product still adhering. The washing is carried out in such a way that the desired products adhering in each case to the catalyst can be removed therefrom but temperature and pressure are not chosen so high that the generally organic coatings are likewise removed. Preferably, the catalyst is washed only with a suitable solvent. Thus, all solvents in which the respective reaction product is readily soluble are suitable for this washing process. The amount of solvent used and the duration of the washing process are not critical. The washing process can be repeated several times and can be carried out at elevated temperatures. When $CO_2$ is used as the solvent, supercritical pressure is preferred; otherwise, the washing process can be carried out under atmospheric, superatmospheric or supercritical pressure. After the end of the washing process, the catalyst is generally dried. Although the drying process is not generally critical, the drying temperature should not too greatly exceed the boiling point of the solvent used for the washing, in order to avoid abrupt evaporation of the solvent in the pores, in particular in the micropores, since this too may lead to damage to the catalyst.

In a possible preferred embodiment for the preparation of the process, the novel, continuous process for the synthesis of TEDA need not be interrupted during the regeneration of the novel catalyst, in order to increase the throughput in the process. This can be achieved by the use of at least two reactors which are connected in parallel and which can be operated alternately.

The catalyst regeneration can be carried out in such a way that at least one of the reactors connected in parallel is decoupled from the respective reaction stage and the catalyst contained in this reactor is regenerated, at least one reactor for the reaction of PIP always being available in each stage in the course of the continuous process.

The TEDA obtained according to the invention can be recrystallized from suitable solvents (e.g. pentane or hexane) in order to improve its purity. However, this is not generally required since TEDA can be prepared with purities greater than 95% by weight, for example greater than 97% by weight, by the novel process.

In a particular embodiment, the TEDA preparation process as claimed in the claims is combined with the subsequent TEDA process according to the prior EP Application No. 00114475.7 of Jul. 6, 2000 (BASF AG).

According to this combination, first TEDA is prepared as claimed in the claims. In the subsequent working-up of the TEDA (for example by distillation), which can be carried out in a plurality of stages, the TEDA is vaporized, preferably in the last working-up stage (in particular distillation or rectification), and the TEDA vapor obtained, for example, at the top or in a side take-off of the distillation column and preferably having a purity of greater than 95, in particular greater than 97, % by weight is passed into a liquid solvent. This passage of the TEDA vapor directly into a liquid solvent is also referred to below as a TEDA quench.

By subsequent crystallization of the TEDA from the solution thus obtained, pure TEDA of high quality is obtained.

The liquid solvent is generally chosen from the group consisting of cyclic or acyclic hydrocarbons, chlorinated aliphatic hydrocarbons, aromatic hydrocarbons, alcohols, ketones, aliphatic carboxylic esters, aliphatic nitriles and ethers.

For the preparation of a solution of pure TEDA according to the above process combination, which can be used, for example, as a catalyst solution in the preparation of polyurethane foam, a preferably used solvent for the TEDA quench is an alcohol (e.g. ethylene glycol, 1,4-butanediol or preferably dipropylene glycol). The color number of a resulting 33% strength TEDA solution in dipropylene glycol is less than 150 APHA, in particular less than 100 APHA, very particularly less than 50 APHA.

For the preparation of pure (crystalline) TEDA according to the above process combination, an aliphatic hydrocarbon, in particular a saturated aliphatic hydrocarbon of 5 to 8 carbon atoms (e.g. hexane, heptane or preferably pentane) was preferably used as a solvent for the TEDA quench. The crystallization of the pure TEDA from the TEDA solution prepared according to the invention can be effected by the methods known to a person skilled in the art. The TEDA crystals obtained by a subsequent multistage, or preferably one-stage, crystallization are of high purity (purity of in general at least 99.5, in particular at least 99.8, % by weight, PIP content of less than 0.1, in particular less than 0.05, % by weight, N-ethylpiperazine content less than 0.02, in particular less than 0.01, % by weight) and the color number of a 33% strength by weight solution in dipropylene glycol is less than 50 APHA, in particular less than 30 APHA.

(All APHA numbers according to DIN ISO 6271).

The passage of the TEDA vapor in the liquid solvent is carried out in a quench apparatus, for example preferably in a falling-film condenser (thin-film, spray or downflow condenser) or in a nozzle apparatus. The TEDA vapor can be fed cocurrently or countercurrently to the liquid solvent. It is advantageous to pass the TEDA vapor into the quench apparatus from above. Tangential feeding of the liquid solvent at the top of the falling-film condenser or feeding of the liquid solvent through one or more nozzles is furthermore advantageous for achieving complete wetting of the inner surface of the quench apparatus.

In general, the temperature in the TEDA quench is brought to 20 to 100° C., preferably 30 to 60° C., by heating the solvent used and/or the quench apparatus. Absolute pressure in the TEDA quench is in general from 0.5 to 1.5 bar.

In general, depending on the type of the solvent, solutions having a TEDA content of from about 1 to 50, preferably from 20 to 40, % by weight are first obtained in the TEDA quench.

The novel process is carried out at a reaction temperature of from 250 to 500° C., preferably from 300 to 400° C., in particular from 330 to 400° C. The pressures used are from 0.01 to 50, preferably from 0.5 to 20, bar, in particular atmospheric pressure. The resulting pressure drop across the catalyst bed is not included in these values. PIP is generally used as a mixture with water, preferably at least 10, in particular from 20 to 60, % by weight of water being present in the mixture.

The novel process can be carried out batchwise or, preferably, continuously.

The novel reaction can be carried out in the liquid phase or, preferably, in the gas phase.

The reaction is preferably carried out in the presence of a solvent or diluent.

Examples of suitable solvents or diluents are acyclic or cyclic ethers of 2 to 12 carbon atoms, such as dimethyl ether, diethyl ether, di-n-propyl ether or isomers thereof, MTBE, THF or pyran, or lactones, such as gamma-butyrolactone, polyethers, such as monoglyme, diglyme, etc., aromatic or aliphatic hydrocarbons, such as benzene, toluene, xylene, pentane, cyclopentane, hexane and petroleum ether, or mixtures thereof and in particular also N-methylpyrrolidone (NMP) or water or aqueous organic solvents or diluents of the abovementioned type. Ammonia is furthermore a suitable solvent or diluent.

A particularly preferred solvent or diluent, in particular solvent, is water.

Other suitable diluents for carrying out the reaction in the gas phase are inert gases, such as nitrogen (for example over and above the saturation of the reactor feed) or argon. Preferably, the reaction is carried out in a gas phase in the presence of ammonia.

The TEDA selectivity which can be achieved with the novel process is up to >90%.

The starting components or the reactor feed are or is advantageously preheated.

Furthermore, the following reaction conditions have proven advantageous for carrying out the novel process:
  a WHSV (weight hourly space velocity), based on amines used in the reaction, of from 0.01 to 6 $h^{-1}$, preferably from 0.05 to 1 $h^{-1}$, particularly preferably from 0.1 to 1 $h^{-1}$.

Suitable reactors in which the novel process is carried out are stirred containers, in particular tubular reactors and tube-bundle reactors.

The zeolite catalyst is arranged in the reactor preferably as a fixed bed.

The reaction in the liquid phase can be carried out, for example, by the suspension, trickle-bed or liquid-phase procedure.

The preferred reaction in the gas phase can be carried out in a fluidized catalyst bed or, preferably, a fixed catalyst bed.

The following paragraph additionally describes, by way of example, the manner in which the novel process can be carried out:

The reactor feed (composition: as described above) is converted into the gas phase in an evaporator, which may be part of the actual reactor, at a temperature of 250–500° C., and is passed over the catalyst. The reaction discharge obtained in gaseous form at the reactor exit is quenched at 20–100° C., preferably at 80° C., by liquefied reaction discharge circulated by pumping. This liquefied reaction discharge is worked up as follows: In a first distillation stage, low boilers, such as acetaldehyde, ethylamine, ammonia and water, and heterocyclic compounds which are formed as byproducts in the synthesis are separated off.

In a second distillation stage, the reaction discharge is freed from piperazine, which is recycled to the reactor feed. The stream of the piperazine separated off may contain up to 20% by weight of TEDA. (Alternatively, it is also possible to separate off water and piperazine simultaneously, which can be recycled together to the reactor feed.) In a third distillation stage, the desired product TEDA is obtained from the reaction discharge by distillation and, if required, is further worked up, for example in a downstream crystallization stage (for example as described further below).

Inter alia, the following advantages are achieved using the novel process:
  only a single starting material (PIP) is used
  small excess of water in the feed (<60% by weight)
  high PIP conversion (>80%)
  high TEDA selectivity (>90%)
  simpler working-up of the TEDA since less EtPIP is formed
  long catalyst on-stream time (>1000 h), catalyst can be regenerated.

The novel process can also be carried out using a substituted piperazine, for example aminoethylpiperazine, bis(aminoethyl)piperazine, hydroxyethylpiperazine or bis(hydroxyethyl)piperazine. However, the advantage according to the invention, whereby the synthesis of the substituted piperazines is unnecessary, is then no longer present.

Since the formation of the undesired byproduct EtPIP occurs only to a minor extent as a result of using the catalysts described above, the TEDA synthesis from PIP can be carried out under conditions which give a higher conversion. In particular, the conversion can be increased by higher reaction temperatures. Owing to the higher conversion, smaller recycle streams of PIP are present and furthermore the cost of purifying the end product TEDA is reduced. The PIP conversion achievable by the novel process is above 80%, preferably from 60 to 75%.

The examples which follow illustrate the invention.

EXAMPLES

A Catalyst Preparation

The zeolite powder (from ALSIPENTA, aluminosilicate of the type Na-ZSM-5, modulus 1 000) was subjected to an exchange three times with a 20% strength $NH_4Cl$ solution, washed, and calcined at 500° C. for 5 hours. Thereafter, the powder was subjected to an acid treatment (5% strength HCl, room temperature) three times for 8 hours, washed neutral each time with water and calcined at 500° C. for 3 hours. Finally, the zeolite powder was extruded with 20% by weight of $SiO_2$ (based on the total mass of the prepared 2 mm extrudates) and was calcined at 500° C. for 5 hours.

B Carrying Out the Process

The catalysts were used in a gas-phase apparatus (heated tubular reactor; length: 1000 mm, diameter 6 mm). Mixture of starting materials: 50% of PIP, 50.0% of water (all data in % by weight). The aqueous mixture of starting materials was pumped directly into the reactor and vaporized into the upper part at a reaction temperature of 350° C. or 370° C. before it was passed under atmospheric pressure over the catalyst. Space velocity: 0.2 kg of mixture of starting materials/kg of catalyst-h. The reaction products were condensed in a condenser at the reactor exit and were collected, and an aliquot part was analyzed by gas chromatography.

GC Analysis:
  Column: RTX-5, 30 m; temperature program: 80° C.–5° C./min–280° C., detector: FID.

TABLE 1

Synthesis of triethylenediamine (TEDA) from piperazine (PIP)

| Example | Catalyst | Modulus [SiO2/Al2O3] | WHSV [$h^{-1}$] | Temp. [° C.] | $C_{PIP}$ [%] | $S_{TEDA}$ [%] | $S_{Et-PIP}$ [%] |
|---|---|---|---|---|---|---|---|
| 1 | A (SKO 325) | 1000 | 0.1 | 370 | 71 | 88 | 0.3 |
| 2 | A (SKO 325) | 1000 | 0.1 | 350 | 60 | 88 | 0.2 |
| 3*) | H-ZSM 5 | 90 | ~0.5 | 340 | 43 | 91 | 0.80 |
| 4*) | H-ZSM 5 | 31 | ~0.5 | 310 | 18 | 92 | 0.21 |
| 5*) | H-ZSM 5 | 31 | ~0.5 | 340 | 66 | 88 | 0.91 |

*)Comparative example: EP 312734, table on page 6, entry no. 5, 3 and 6; 3 bar PIP:$H_2O$ = 40:60% by weight

What is claimed is:

1. A process for the preparation of triethylenediamine by reacting piperazine over a zeolite catalyst which, in addition to SiO2, contains an oxide of at least one further divalent, trivalent or tetravalent metal M, wherein the zeolite has a molar Si/M ratio of >100.

2. A process as claimed in claim 1, wherein M is selected from the group consisting of Al, B, Fe, Co, Ni, V, Mo, Mn, As, Sb, Bi, La, Ga, In, Y, Sc, Cr, Zn, Sn, Be, Ti, Zr, Ge and Hf.

3. A process as claimed in claim 2, wherein M is selected from the group consisting of B, Al, Fe, Ga, Ti and Ge.

4. A process as claimed in claim 2, wherein M is Al.

5. A process as claimed in claim 1, wherein the zeolite catalyst has a molar Si/M ratio of >200.

6. A process as claimed in claim 5, wherein the Si/M ratio is from 300 to 40 000.

7. A process as claimed in claim 5, wherein the Si/M ratio is from 400 to 5 000.

8. A process as claimed in claim 1, wherein a zeolite of the Pentasil type is used.

9. A process as claimed in claim 8, wherein a zeolite of the ZSM-5 or ZSM-11 type or a mixed structure thereof, is used.

10. A process as claimed in claim 1, wherein the catalyst is used at least partly in the H form.

11. A process as claimed in claim 1, which is carried out at from 250 to 500° C., and at from 0.01 to 50 bar, plus the resulting pressure drop across the catalyst bed.

12. A process as claimed in claim 11, wherein the process is carried out at atmospheric pressure.

13. A process as claimed in claim 1, wherein piperazine is used as a mixture with water and/or an organic diluent.

14. A process as claimed in claim 1, wherein the piperazine conversion is more than 80%.

15. A process as claimed in claim 1, which is carried out batchwise or continuously.

16. A process as claimed in claim 15, wherein the process is carried out continuously.

17. A process as claimed in claim 15, wherein the process is carried out in the gas phase.

18. A process as claimed in claim 15, wherein the process is carried out over a fluidized catalyst bed or a fixed catalyst bed.

* * * * *